(12) United States Patent
Brahmachari et al.

(10) Patent No.: US 7,657,378 B1
(45) Date of Patent: Feb. 2, 2010

(54) COMPUTER BASED METHOD FOR IDENTIFYING PEPTIDES USEFUL AS DRUG TARGETS

(75) Inventors: Samir Kumar Brahmachari, Delhi (IN); Debasis Dash, Delhi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/539,032

(22) Filed: Mar. 30, 2000

(51) Int. Cl.
G06F 19/00 (2006.01)
(52) U.S. Cl. ...................................... 702/19
(58) Field of Classification Search .................. 702/20, 702/27; 703/2
See application file for complete search history.

(56) References Cited

OTHER PUBLICATIONS

Bansal,"An automated comparative analysis of 17 complete microgial genomes", Bioinformatics, vol. 15 No. 11(1999) pp. 900-908.*
McGuire et al.,"Conservation of DNA Regulatory Motifs and Discovery of New Motifs in Microbial Genomes", Genome Research, vol. 10 (2000) pp. 744-757.*
Pietrokovski, "Searching databased of conserved sequence regions by aligning protein multiple-alignments", Nucleic Acids Research, vol. 24 No. 19 (1996) pp. 3836-3845.*
Plikaytis et al. Journal of General Microbiology. 1992. vol. 138, No. 11, pp. 2265-2273.*
Wilbur et al. PNAS. Feb. 1983. vol. 80, No. 3, pp. 726-730.*
American Heritage Dictionary of the English Language, Fourth Edition, definition of "genome". Found at www.bartleby.com, printed Sep. 17, 2006.*
Merriam-Wbster Online Dictionary, definition of "genome". Found at http://m-w.com, printed Sep. 17, 2006.*
Oxford English Dictionary Online, definition of "genome". Found at http://dictionary.oed.com, printed Sep. 17, 2006.*
Bruccoleri et al. (Nucleic Acids Research (1998) vol. 26, No. 19, pp. 4482-4486).*
Galperin et al. (Current Opinion in Biotechnology (1999) vol. 10, pp. 571-578.*
Gray et al. (CMLS (1999) vol. 56, pp. 779-787.*
Hobohm et al. (Journal of Molecular Biology (1995) vol. 251, pp. 390-399.*
Rosamond et al. (Science (2000) vol. 287, pp. 1973-1976.*
GenBANK Accession No. YP 001285950.*
Altschul et al., "Basic Local Alignment Search Tool"; *J. Mol. Biol.*, vol. 215, No. 3; pp. 403-410.
Cutler et al., "TOR kinase homologs function in a signal transduction pathway that is conserved from yeast to mammals"; *Molecular and Cellular Endocrinology*, vol. 155, Nos. 1-2; pp. 135-142 (1999).

Ghannoum et al., "Antifungal Agents: Mode of Action, Mechanisms of Resistance, and Correlation of These Mechanisms with Bacterial Resistance"; *Clinical Microbiology Reviews*, vol. 12, No. 4; pp. 501-517 (1999).
McCafferty et al., "Synergy and duality in peptide antibiotic mechanisms"; Chemical Biology, vol. 3, No. 5; pp. 672-680 (1999).
Porse et al., "Ribosomal Mechanics, Antibodies, and GTP Hydrolysis"; *Cell*, vol. 97; pp. 423-426 (1999).
Presnell et al., "A Segment-Based Approach to Protein Secondary Structure Prediction"; *Biochemistry*, vol. 31, No. 4; pp. 983-993 (1992).
Rooman et al., "Identification of predictive sequence motifs limited by protein structure data base size"; *Nature*, vol. 335, No. 6185; pp. 45-49 (1988).
Wilbur et al., "Rapid similarity searches of nucleic acid and protein data banks"; *Proc. Natl. Acad. Sci USA*, vol. 80, No. 3; pp. 726-730 (1983).
Wimberly et al., "A Detailed View of a Ribosomal Active Site: The Structure of the L11-RNA Complex"; Cell, vol. 97, No. 4; pp. 492-502 (1999).
Cole et al. Nature. 393(6685):537-544 (1998).
Kunst et al. Nature. 390(6657):249-256 (1997).
Fraser et al. Science. 270(5235):397-403 (1995).
Himmelreich et al. Nucleic Acids Res. 24(22):4420-4449 (1996).
Blattner et al. Science. 277(5531):1453-1474 (1997).
Tomb et al. Nature. 388(6642):539-547 (1997).
Fleischmann et al. Science. 269(5223):496-512 (1995).
Tatusov, et al. "The COG database: a tool for genomre-scale analysis of protein functions and evolution" Nucleic Acids Research. vol. 28. No. 1. pp. 33-36 (2000).
Werner-Washbume, et al. "Comparative analysis of multiple genome-scale data sets." Genome Research. 12:1564-1573 (2002).
Koonin, et al. "Protein sequence comparison at genome scale." Methods in Enzymology. vol. 266. pp. 295-322 (1996).

* cited by examiner

*Primary Examiner*—Lori A Clow
(74) *Attorney, Agent, or Firm*—Knobbe, Martens, Olson & Bear, LLP

(57) ABSTRACT

The present invention relates to a novel computer based method for performing genome-wise comparison of several organisms, the said computational method involves creation of peptide libraries from protein sequences of several organisms and subsequent comparison leading to identification of conserved invariant peptide motifs, and to this end several invariant peptide motifs have been identified by direct sequence comparison between various bacterial organisms and host genomes without any a priori assumptions, and the present method is useful for identification of potential drug targets and can serve as drug screen for broad-spectrum antibacterials as well as for specific diagnosis of infections, and in addition, for assignment of function to proteins of yet unknown functions with the help of such invariant peptide motif signatures.

8 Claims, 4 Drawing Sheets

```
                        SEQUENCE LISTING

<160> NUMBER OF SEQ ID NOS: 69

<210> SEQ ID NO 1
<211> LENGTH: 13
<212> TYPE: PRT
<213> ORGANISM: Mycoplasma pneumoniae

<400> SEQUENCE: 1

Ala Ala Gln Ser Ile Gly Glu Pro Gly Thr Gln Leu Thr
 1               5                  10

<210> SEQ ID NO 2
<211> LENGTH: 9
<212> TYPE: PRT
<213> ORGANISM: Mycoplasma pneumoniae

<400> SEQUENCE: 2

Ala Gly Asp Gly Thr Thr Thr Ala Thr
 1               5

<210> SEQ ID NO 3
<211> LENGTH: 8
<212> TYPE: PRT
<213> ORGANISM: Mycoplasma pneumoniae

<400> SEQUENCE: 3

Ala Gly Arg His Gly Asn Lys Gly
 1               5

<210> SEQ ID NO 4
<211> LENGTH: 10
```

```
<212> TYPE: PRT
<213> ORGANISM: Mycoplasma pneumoniae

<400> SEQUENCE: 4

Ala His Ile Asp Ala Gly Lys Thr Thr Thr
1               5                   10

<210> SEQ ID NO 5
<211> LENGTH: 8
<212> TYPE: PRT
<213> ORGANISM: Mycoplasma pneumoniae

<400> SEQUENCE: 5

Cys Pro Ile Glu Thr Pro Glu Gly
1               5

<210> SEQ ID NO 6
<211> LENGTH: 8
<212> TYPE: PRT
<213> ORGANISM: Mycoplasma pneumoniae

<400> SEQUENCE: 6

Asp Glu Pro Ser Ile Gly Leu His
1               5

<210> SEQ ID NO 7
<211> LENGTH: 8
<212> TYPE: PRT
<213> ORGANISM: Mycoplasma pneumoniae

<400> SEQUENCE: 7

Asp Glu Pro Thr Ser Ala Leu Asp
1               5

<210> SEQ ID NO 8
<211> LENGTH: 10
<212> TYPE: PRT
<213> ORGANISM: Mycoplasma pneumoniae

<400> SEQUENCE: 8

Asp Glu Pro Thr Thr Ala Leu Asp Val Thr
1               5                   10

<210> SEQ ID NO 9
<211> LENGTH: 8
<212> TYPE: PRT
<213> ORGANISM: Mycoplasma pneumoniae

<400> SEQUENCE: 9

Asp His Ala Gly Ile Ala Thr Gln
1               5

<210> SEQ ID NO 10
<211> LENGTH: 9
<212> TYPE: PRT
<213> ORGANISM: Mycoplasma pneumoniae

<400> SEQUENCE: 10

Asp His Pro His Gly Gly Gly Glu Gly
1               5

<210> SEQ ID NO 11
<211> LENGTH: 8
<212> TYPE: PRT
<213> ORGANISM: Mycoplasma pneumoniae
```

-continued

```
<400> SEQUENCE: 11

Asp Leu Gly Gly Gly Thr Phe Asp
1               5

<210> SEQ ID NO 12
<211> LENGTH: 9
<212> TYPE: PRT
<213> ORGANISM: Mycoplasma pneumoniae

<400> SEQUENCE: 12

Asp Val Leu Asp Thr Trp Phe Ser Ser
1               5

<210> SEQ ID NO 13
<211> LENGTH: 8
<212> TYPE: PRT
<213> ORGANISM: Mycoplasma pneumoniae

<400> SEQUENCE: 13

Glu Arg Glu Arg Gly Ile Thr Ile
1               5

<210> SEQ ID NO 14
<211> LENGTH: 11
<212> TYPE: PRT
<213> ORGANISM: Mycoplasma pneumoniae

<400> SEQUENCE: 14

Glu Arg Gly Ile Thr Ile Thr Ser Ala Ala Thr
1               5                   10

<210> SEQ ID NO 15
<211> LENGTH: 12
<212> TYPE: PRT
<213> ORGANISM: Mycoplasma pneumoniae

<400> SEQUENCE: 15

Glu Ser Arg Arg Ile Asp Asn Gln Leu Arg Gly Arg
1               5                   10

<210> SEQ ID NO 16
<211> LENGTH: 8
<212> TYPE: PRT
<213> ORGANISM: Mycoplasma pneumoniae

<400> SEQUENCE: 16

Phe Ser Gly Gly Gln Arg Gln Arg
1               5

<210> SEQ ID NO 17
<211> LENGTH: 9
<212> TYPE: PRT
<213> ORGANISM: Mycoplasma pneumoniae

<400> SEQUENCE: 17

Gly Glu Pro Gly Val Gly Lys Thr Ala
1               5

<210> SEQ ID NO 18
<211> LENGTH: 8
<212> TYPE: PRT
<213> ORGANISM: Mycoplasma pneumoniae

<400> SEQUENCE: 18
```

```
Gly Phe Asp Tyr Leu Arg Asp Asn
  1               5

<210> SEQ ID NO 19
<211> LENGTH: 8
<212> TYPE: PRT
<213> ORGANISM: Mycoplasma pneumoniae

<400> SEQUENCE: 19

Gly His Asn Leu Gln Glu His Ser
  1               5

<210> SEQ ID NO 20
<211> LENGTH: 9
<212> TYPE: PRT
<213> ORGANISM: Mycoplasma pneumoniae

<400> SEQUENCE: 20

Gly Ile Asp Leu Gly Thr Thr Asn Ser
  1               5

<210> SEQ ID NO 21
<211> LENGTH: 10
<212> TYPE: PRT
<213> ORGANISM: Mycoplasma pneumoniae

<400> SEQUENCE: 21

Gly Ile Asn Leu Leu Arg Glu Gly Leu Asp
  1               5                  10

<210> SEQ ID NO 22
<211> LENGTH: 11
<212> TYPE: PRT
<213> ORGANISM: Mycoplasma pneumoniae

<400> SEQUENCE: 22

Gly Ile Val Gly Leu Pro Asn Val Gly Lys Ser
  1               5                  10

<210> SEQ ID NO 23
<211> LENGTH: 8
<212> TYPE: PRT
<213> ORGANISM: Mycoplasma pneumoniae

<400> SEQUENCE: 23

Gly Lys Ser Ser Leu Leu Asn Ala
  1               5

<210> SEQ ID NO 24
<211> LENGTH: 13
<212> TYPE: PRT
<213> ORGANISM: Mycoplasma pneumoniae

<400> SEQUENCE: 24

Gly Leu Thr Gly Arg Lys Ile Ile Val Asp Thr Tyr Gly
  1               5                  10

<210> SEQ ID NO 25
<211> LENGTH: 11
<212> TYPE: PRT
<213> ORGANISM: Mycoplasma pneumoniae

<400> SEQUENCE: 25

Gly Pro Pro Gly Thr Gly Lys Thr Leu Leu Ala
```

```
<210> SEQ ID NO 26
<211> LENGTH: 8
<212> TYPE: PRT
<213> ORGANISM: Mycoplasma pneumoniae

<400> SEQUENCE: 26

Gly Pro Pro Gly Val Gly Lys Thr
1               5

<210> SEQ ID NO 27
<211> LENGTH: 8
<212> TYPE: PRT
<213> ORGANISM: Mycoplasma pneumoniae

<400> SEQUENCE: 27

Gly Ser Gly Lys Thr Thr Leu Leu
1               5

<210> SEQ ID NO 28
<211> LENGTH: 8
<212> TYPE: PRT
<213> ORGANISM: Mycoplasma pneumoniae

<400> SEQUENCE: 28

Gly Thr Arg Ile Phe Gly Pro Val
1               5

<210> SEQ ID NO 29
<211> LENGTH: 10
<212> TYPE: PRT
<213> ORGANISM: Mycoplasma pneumoniae

<400> SEQUENCE: 29

Ile Asp Thr Pro Gly His Val Asp Phe Thr
1               5                   10

<210> SEQ ID NO 30
<211> LENGTH: 12
<212> TYPE: PRT
<213> ORGANISM: Mycoplasma pneumoniae

<400> SEQUENCE: 30

Ile Ile Ala His Ile Asp His Gly Lys Ser Thr Leu
1               5                   10

<210> SEQ ID NO 31
<211> LENGTH: 9
<212> TYPE: PRT
<213> ORGANISM: Mycoplasma pneumoniae

<400> SEQUENCE: 31

Ile Asn Gly Phe Gly Arg Ile Gly Arg
1               5

<210> SEQ ID NO 32
<211> LENGTH: 9
<212> TYPE: PRT
<213> ORGANISM: Mycoplasma pneumoniae

<400> SEQUENCE: 32

Ile Arg Glu Gly Gly Arg Thr Val Gly
1               5
```

```
<210> SEQ ID NO 33
<211> LENGTH: 10
<212> TYPE: PRT
<213> ORGANISM: Mycoplasma pneumoniae

<400> SEQUENCE: 33

Ile Val Gly Glu Ser Gly Ser Gly Lys Ser
 1               5                  10

<210> SEQ ID NO 34
<211> LENGTH: 10
<212> TYPE: PRT
<213> ORGANISM: Mycoplasma pneumoniae

<400> SEQUENCE: 34

Lys Phe Ser Thr Tyr Ala Thr Trp Trp Ile
 1               5                  10

<210> SEQ ID NO 35
<211> LENGTH: 8
<212> TYPE: PRT
<213> ORGANISM: Mycoplasma pneumoniae

<400> SEQUENCE: 35

Lys Met Ser Lys Ser Lys Gly Asn
 1               5

<210> SEQ ID NO 36
<211> LENGTH: 8
<212> TYPE: PRT
<213> ORGANISM: Mycoplasma pneumoniae

<400> SEQUENCE: 36

Lys Met Ser Lys Ser Leu Gly Asn
 1               5

<210> SEQ ID NO 37
<211> LENGTH: 17
<212> TYPE: PRT
<213> ORGANISM: Mycoplasma pneumoniae

<400> SEQUENCE: 37

Lys Asn Met Ile Thr Gly Ala Ala Gln Met Asp Gly Ala Ile Leu Val
 1               5                  10                  15

Val

<210> SEQ ID NO 38
<211> LENGTH: 8
<212> TYPE: PRT
<213> ORGANISM: Mycoplasma pneumoniae

<400> SEQUENCE: 38

Lys Pro Asn Ser Ala Leu Arg Lys
 1               5

<210> SEQ ID NO 39
<211> LENGTH: 11
<212> TYPE: PRT
<213> ORGANISM: Mycoplasma pneumoniae

<400> SEQUENCE: 39

Leu Phe Gly Gly Ala Gly Val Gly Lys Thr Val
 1               5                  10
```

```
<210> SEQ ID NO 40
<211> LENGTH: 8
<212> TYPE: PRT
<213> ORGANISM: Mycoplasma pneumoniae

<400> SEQUENCE: 40

Leu Gly Pro Ser Gly Cys Gly Lys
 1               5

<210> SEQ ID NO 41
<211> LENGTH: 8
<212> TYPE: PRT
<213> ORGANISM: Mycoplasma pneumoniae

<400> SEQUENCE: 41

Leu His Ala Gly Gly Lys Phe Asp
 1               5

<210> SEQ ID NO 42
<211> LENGTH: 13
<212> TYPE: PRT
<213> ORGANISM: Mycoplasma pneumoniae

<400> SEQUENCE: 42

Leu Ile Asp Glu Ala Arg Thr Pro Leu Ile Ile Ser Gly
 1               5                  10

<210> SEQ ID NO 43
<211> LENGTH: 9
<212> TYPE: PRT
<213> ORGANISM: Mycoplasma pneumoniae

<400> SEQUENCE: 43

Leu Leu Asn Arg Ala Pro Thr Leu His
 1               5

<210> SEQ ID NO 44
<211> LENGTH: 11
<212> TYPE: PRT
<213> ORGANISM: Mycoplasma pneumoniae

<400> SEQUENCE: 44

Leu Pro Asp Lys Ala Ile Asp Leu Ile Asp Glu
 1               5                  10

<210> SEQ ID NO 45
<211> LENGTH: 8
<212> TYPE: PRT
<213> ORGANISM: Mycoplasma pneumoniae

<400> SEQUENCE: 45

Leu Pro Gly Lys Leu Ala Asp Ser
 1               5

<210> SEQ ID NO 46
<211> LENGTH: 8
<212> TYPE: PRT
<213> ORGANISM: Mycoplasma pneumoniae

<400> SEQUENCE: 46

Leu Ser Gly Gly Gln Gln Gln Arg
 1               5

<210> SEQ ID NO 47
```

```
<211> LENGTH: 9
<212> TYPE: PRT
<213> ORGANISM: Mycoplasma pneumoniae

<400> SEQUENCE: 47

Met Gly His Val Asp His Gly Lys Thr
1               5

<210> SEQ ID NO 48
<211> LENGTH: 12
<212> TYPE: PRT
<213> ORGANISM: Mycoplasma pneumoniae

<400> SEQUENCE: 48

Asn Ala Asp Phe Asp Gly Asp Gln Met Ala Val His
1               5                   10

<210> SEQ ID NO 49
<211> LENGTH: 8
<212> TYPE: PRT
<213> ORGANISM: Mycoplasma pneumoniae

<400> SEQUENCE: 49

Asn Gly Ala Gly Lys Ser Thr Leu
1               5

<210> SEQ ID NO 50
<211> LENGTH: 8
<212> TYPE: PRT
<213> ORGANISM: Mycoplasma pneumoniae

<400> SEQUENCE: 50

Asn Leu Leu Gly Lys Arg Val Asp
1               5

<210> SEQ ID NO 51
<211> LENGTH: 8
<212> TYPE: PRT
<213> ORGANISM: Mycoplasma pneumoniae

<400> SEQUENCE: 51

Asn Thr Asp Ala Glu Gly Arg Leu
1               5

<210> SEQ ID NO 52
<211> LENGTH: 11
<212> TYPE: PRT
<213> ORGANISM: Mycoplasma pneumoniae

<400> SEQUENCE: 52

Pro Ser Ala Val Gly Tyr Gln Pro Thr Leu Ala
1               5                   10

<210> SEQ ID NO 53
<211> LENGTH: 8
<212> TYPE: PRT
<213> ORGANISM: Mycoplasma pneumoniae

<400> SEQUENCE: 53

Gln Arg Val Ala Ile Ala Arg Ala
1               5

<210> SEQ ID NO 54
<211> LENGTH: 9
<212> TYPE: PRT
```

-continued

<213> ORGANISM: Mycoplasma pneumoniae

<400> SEQUENCE: 54

Gln Arg Tyr Lys Gly Leu Gly Glu Met
1               5

<210> SEQ ID NO 55
<211> LENGTH: 10
<212> TYPE: PRT
<213> ORGANISM: Mycoplasma pneumoniae

<400> SEQUENCE: 55

Arg Asp Gly Leu Lys Pro Val His Arg Arg
1               5                   10

<210> SEQ ID NO 56
<211> LENGTH: 9
<212> TYPE: PRT
<213> ORGANISM: Mycoplasma pneumoniae

<400> SEQUENCE: 56

Ser Ala Leu Asp Val Ser Ile Gln Ala
1               5

<210> SEQ ID NO 57
<211> LENGTH: 8
<212> TYPE: PRT
<213> ORGANISM: Mycoplasma pneumoniae

<400> SEQUENCE: 57

Ser Gly Gly Leu His Gly Val Gly
1               5

<210> SEQ ID NO 58
<211> LENGTH: 8
<212> TYPE: PRT
<213> ORGANISM: Mycoplasma pneumoniae

<400> SEQUENCE: 58

Ser Gly Ser Gly Lys Ser Ser Leu
1               5

<210> SEQ ID NO 59
<211> LENGTH: 8
<212> TYPE: PRT
<213> ORGANISM: Mycoplasma pneumoniae

<400> SEQUENCE: 59

Ser Gly Ser Gly Lys Ser Thr Leu
1               5

<210> SEQ ID NO 60
<211> LENGTH: 15
<212> TYPE: PRT
<213> ORGANISM: Mycoplasma pneumoniae

<400> SEQUENCE: 60

Ser Val Phe Ala Gly Val Gly Glu Arg Thr Arg Glu Gly Asn Asp
1               5                   10                  15

<210> SEQ ID NO 61
<211> LENGTH: 10
<212> TYPE: PRT
<213> ORGANISM: Mycoplasma pneumoniae

<400> SEQUENCE: 61

Thr Gly Arg Thr His Gln Ile Arg Val His
1               5                   10

<210> SEQ ID NO 62
<211> LENGTH: 9
<212> TYPE: PRT
<213> ORGANISM: Mycoplasma pneumoniae

<400> SEQUENCE: 62

Thr Gly Val Ser Gly Ser Gly Lys Ser
1               5

<210> SEQ ID NO 63
<211> LENGTH: 10
<212> TYPE: PRT
<213> ORGANISM: Mycoplasma pneumoniae

<400> SEQUENCE: 63

Thr Leu Ser Gly Gly Glu Ala Gln Arg Ile
1               5                   10

<210> SEQ ID NO 64
<211> LENGTH: 9
<212> TYPE: PRT
<213> ORGANISM: Mycoplasma pneumoniae

<400> SEQUENCE: 64

Thr Asn Lys Tyr Ala Glu Gly Tyr Pro
1               5

<210> SEQ ID NO 65
<211> LENGTH: 9
<212> TYPE: PRT
<213> ORGANISM: Mycoplasma pneumoniae

<400> SEQUENCE: 65

Thr Pro Arg Ser Asn Pro Ala Thr Tyr
1               5

<210> SEQ ID NO 66
<211> LENGTH: 8
<212> TYPE: PRT
<213> ORGANISM: Mycoplasma pneumoniae

<400> SEQUENCE: 66

Val Glu Gly Asp Ser Ala Gly Gly
1               5

<210> SEQ ID NO 67
<211> LENGTH: 10
<212> TYPE: PRT
<213> ORGANISM: Mycoplasma pneumoniae

<400> SEQUENCE: 67

Val Arg Lys Arg Pro Gly Met Tyr Ile Gly
1               5                   10

<210> SEQ ID NO 68
<211> LENGTH: 147
<212> TYPE: PRT
<213> ORGANISM: Mycobacterium tuberculosis

<400> SEQUENCE: 68

```
Met Thr Asp Asp Pro Gly Ser Gly Phe Thr Thr Val Trp Asn Ala Val
 1               5                  10                  15

Val Ser Glu Leu Asn Gly Asp Pro Lys Val Asp Asp Gly Pro Ser Ser
             20                  25                  30

Asp Ala Asn Leu Ser Ala Pro Leu Thr Pro Gln Gln Arg Ala Trp Leu
             35                  40                  45

Asn Leu Val Gln Pro Leu Thr Ile Val Glu Gly Phe Ala Leu Leu Ser
 50                  55                  60

Val Pro Ser Ser Phe Val Gln Asn Glu Ile Glu Arg His Leu Arg Ala
65                   70                  75                  80

Pro Ile Thr Asp Ala Leu Ser Arg Arg Leu Gly His Gln Ile Gln Leu
                 85                  90                  95

Gly Val Arg Ile Ala Pro Pro Ala Thr Asp Gly Ala Asp Thr Thr
                 100                 105                 110

Val Pro Pro Ser Glu Asn Pro Ala Thr Thr Ser Pro Asp Thr Thr Asp
                 115                 120                 125

Asn Asp Glu Ile Asp Asp Ser Ala Ala Ala Arg Gly Asp Asn Gln His
 130                 135                 140

Ser Trp Pro
145

<210> SEQ ID NO 69
<211> LENGTH: 142
<212> TYPE: PRT
<213> ORGANISM: Mycobacterium tuberculosis

<400> SEQUENCE: 69

Met Asp Ala Ala Thr Thr Arg Val Gly Leu Thr Asp Leu Thr Phe Arg
 1               5                  10                  15

Leu Leu Arg Glu Ser Phe Ala Asp Ala Val Ser Trp Val Ala Lys Asn
             20                  25                  30

Leu Pro Ala Arg Pro Ala Val Pro Val Leu Ser Gly Val Leu Leu Thr
             35                  40                  45

Gly Ser Asp Asn Gly Leu Thr Ile Ser Gly Phe Asp Tyr Glu Val Ser
 50                  55                  60

Ala Glu Ala Gln Val Gly Ala Glu Ile Val Ser Pro Gly Ser Val Leu
65                   70                  75                  80

Val Ser Gly Arg Leu Leu Ser Asp Ile Thr Arg Ala Leu Pro Asn Lys
                 85                  90                  95

Pro Val Asp Val His Val Glu Gly Asn Arg Val Ala Leu Thr Cys Gly
                 100                 105                 110

Asn Ala Arg Phe Ser Leu Pro Thr Met Pro Val Glu Asp Tyr Pro Thr
                 115                 120                 125

Leu Pro Thr Leu Pro Glu Glu Thr Gly Leu Leu Pro Ala Glu
 130                 135                 140
```

COMPUTER BASED METHOD FOR IDENTIFYING PEPTIDES USEFUL AS DRUG TARGETS

FIELD OF THE INVENTION

This invention relates to a computer-based method for identifying peptides useful as drug targets. More particularly this invention relates to a method for identification of invariant peptide motifs in protein sequence data of various organisms useful as potential drug targets. This invention further provides a method for assignment of function to hypothetical Open Reading Frames (proteins) of unknown function through exact amino acid sequence identity signature.

This invention provides a novel approach for identifying structural and functional signatures of conserved invariant amino acid sequences of proteins that can serve as potential candidates for drug targets. Emergence of drug resistant strains has necessitated identification of new drugs and drug targets. Unique invariant peptide motifs present in the proteins of pathogen but absent in the proteins of host indicate potential drug targets. The invention also provides a method for genome wise comparison of large number of protein sequences simultaneously. Yet another utility is for identifying peptide sequences useful for specific diagnosis of infections.

BACKGROUND OF THE INVENTION

It is known that most of the drugs that are available today to cure infections bind to specific protein target molecules in the cell of the causative organism e.g., several antibiotics are known to disrupt the function of ribosomes so that the protein translation is affected. In these cases it has been found that the drugs either bind to the ribosomal RNA directly or RNA protein complexes (Wimberly et al, 1999). Chemical probing experiments have revealed that the drug binds to certain nucleotide sequences of ribosomal RNA that are 'invariant' in structurally analogous regions in different organisms (Porse and Garrett, 1999). The other class of drugs serves to block other functions such as transcription (Cutler et al, 1999) or fatty acid synthesis in the bacterial cell (McCafferty et al., 1999).

Recently, several drug resistant strains (Ghannoum & Rice, 1999) of pathogenic bacteria have emerged that renders the current treatment procedures ineffective in curing infections due to bacterial pathogens. This necessitates the identification of new drug targets and the corresponding drugs. For this purpose, the availability of complete genome sequences from various microbes offers us an opportunity to analyze all the proteins encoded in a given genome. Since most drugs known today target proteins, it is likely that analyzing all the proteins in a given bacterium may provide new valid drug targets.

The knowledge of conserved invariant sequences in a protein can be useful in understanding certain features of a protein's architecture, such as buried versus exposed location of a segment or the presence of specific secondary structural elements (Rooman and Wodak, 1988, Presnell et al., 1992). The protein's functional role is the most important aspect of conserved invariant sequences. Methods of usual sequence analysis include BLAST (Altschul et al., 1990), and FASTA (Wilbur and Lipman, 1983). These methods carryout sequence alignments whose quality is evaluated using an amino acid substitution matrix. Statistical calculations are performed and the results are output in a ranked manner, with the best similar sequence ranking first. However, these methods are not designed to do a genome-wise comparison simultaneously to identify invariant sequence motifs that are of particular importance in this work.

In order to compare each protein of one organism with all other proteins of several other organisms, either one has to use BLAST one by one or a batch BLAST has to be used which is highly time consuming and therefore not practicable. Even if this were done, at the end of the exercise one would obtain the overall similarity of a set of homologous proteins and alignments.

The problem with multiple sequence alignment is that it is biased to the selection of proteins. Only proteins that are functionally related will give a clear picture of any relationship between the selected proteins. Such procedures are labor intensive and time consuming and leads to results that need further processing and filtering. However, by these methods it is not possible to compare all proteins of several organisms and retrieve conserved invariant peptides.

The present invention provides a novel computer based method to look for invariant sequence motif that will lead to manifold usage as mentioned above and obviates the drawbacks listed above.

The applicants' approach is based on the paradigm that the invariant sequence motifs between the different bacterial proteins must be responsible for an important role for the structure and the function of the protein. Of the numerous ways by which drug targets can be identified, we have taken an approach based on comparative & structural genomics. In this case, the invariant sequence motifs may be either directly or indirectly involved in the function of the subject protein molecule. This approach is derived from the concept that invariant sequence motifs that have remained unchanged across bacteria that are related either distantly or closely should have evolved a unique structural feature that can not be compromised. Indeed, it is even possible that the so-called conservative substitutions are also not tolerated in these invariant sequence motifs. To this end, we have identified several invariant peptide motifs by direct sequence comparison between various bacterial genomes without any a priori assumptions. This purely unbiased and unassumed way of studying the sequences has the benefit of revealing unidentified sequence properties in the various genomes.

Since the invariant sequence motifs may be important for the function of the subject protein molecule, we aim to develop these peptide motifs as potential broad-spectrum antibacterial drug targets. It is probable that a small molecule that can bind specifically to these invariant sequences may cause disruption of function of the subject protein molecule. It is envisaged that this in silico approach will provide new leads for experimental validation to derive functions from protein sequences existing in the available databases.

OBJECTS OF THE INVENTION

The main object of the present invention is to provide a method for genome-wise protein sequence comparison of several organisms and identification of invariant conserved peptides.

Another object of the present invention relates to a novel computer based method for performing genome-wise comparison of several organisms, wherein the said computational method involves creation of peptide libraries from protein sequences of several organisms and subsequent comparison leading to identification of conserved invariant peptide motifs.

Yet another object of the present invention relates to providing a method useful for identification of potential drug targets and can serve as drug screen for broad spectrum antibacterials as well as for specific diagnosis of infection.

Another object of the present invention is to assign suitable function to proteins of yet unknown functions.

Yet another object is to provide a computational method incorporating the invariant peptides or their analogs for identifying potential drug targets.

SUMMARY OF THE INVENTION

The applicants have invented a method to identify invariant peptide motifs, obtained from millions of peptides present in protein sequences of many organisms that has withstood natural selection. These sequences are thus structural determinants of proteins, which could be targeted or can be used as screen as target for drug discovery. These special invariant peptide signatures are also fund to be associated with special functional class of proteins.

The present method will also allow predicting toxicity, alternate target in host cell for drug targeted against a specific peptide motif of a pathogenic organism or any host protein target responsible for a disease process. The method could be extended with lower stringencies to larger number of proteins and also for eukaryotes and multicellular organisms.

Other and further aspects, features and advantages of the present invention will be apparent from the following description of the presently preferred embodiments of the invention given for the purpose of disclosures.

BRIEF DESCRIPTION OF THE COMPUTER PROGRAMS

1. PEPLIB

Objective: To create peptide libraries of organisms from their FASTA format protein files. Thus overlapping peptides of user defined length are generated and then only non-redundant peptides are arranged alphabetically in the output file.

Programming language: PERL on IRIX platform.

2. PEPLIMP

Objective: This program compares the peptide libraries of organisms selected by the user and returns the peptides sequences that are common across the genomes.

Programming language: PERL on IRIX platform.

3. PEPXTRACT

Objective: This program takes peptide file as input, searches in the FASTA format protein files (pep files) and returns the details about the peptides. The details include the PID, location of the peptide in the protein, Organism name etc.

Programming language: PERL on iRIX platform.

4. PEPSTITCH

Objective: This program joins the peptides depending on certain fixed criteria (the two peptides should have the same PID and their locations should be adjacent) and removes overlappings and reports all the conserved invariant peptides.

Programming language: PERL on IRIX platform.

DETAILS OF THE INVENTION

Theoretically speaking, though, a huge number of combinations are possible at amino acid level to form a peptide of a given length only a limited fraction has been observed in biological systems. Out of this limited fraction, only a few peptides remained invariant across the genomes of different organisms. In this work, we sought to answer the question pertaining to the nature of peptides that are invariant across all the pathogenic and nonpathogenic bacterial genome.

In the present invention it has been shown that a stretch of amino acid conservation in proteins of various organisms can provide accurate distinction between different classes of proteins. Generally, these proteins are identified as proteins having very basic function in the survival of the organism.

The protein sequences of several organisms were obtained computationally from the existing databases (NCBI, genbank/genomes/bacteria). These were then chopped computationally into peptide fragments of 'N' amino acid residues by a specially developed computer program PEPLIB. A library of peptides of length 'N' was created for all the proteins of each organism by sliding the window of length 'N' along the sequence by one residue at a time. The peptides thus obtained were computationally sorted in an alphabetical order according to single letter amino acid code, and the redundancy was removed by deleting duplicated peptides. The peptide libraries of various organisms were then compared computationally to find out common peptides. The comparison was done using a specially developed computer program labeled PEPLIMP. The common peptides were located computationally in the original proteins using PEPXTRACT program and were subsequently labeled with their proteins of origin and location. These common peptides were backstitched computationally to form a long chain of common peptides. This was done using PEPSTICH program.

These fragments of common peptides thus obtained were termed as invariant peptides as they originated from functionally conserved proteins. All the conserved invariant peptides obtained from the same protein were then clustered into one group. The secondary structure of these peptides was validated from the protein crystal structure database namely Protein Data Bank (PDB).

Accordingly the invention provides a computer-based method for identifying invariant peptide motifs useful as drug targets wherein the said method comprises the steps of:

i) generating computationally overlapping peptide libraries from all the protein sequences of the selected organisms available in a public database such as one maintained by the National Center for Biotechnology Information (NCBI), ii) sorting computationally the peptides of length 'N' obtained as above, alphabetically, according to single letter amino acid code, iii) matching computationally common peptide sequences of the selected bacteria, iv) locating computationally these common peptides in the original proteins and subsequently labeling them with their origin and location, v) joining computationally the overlapping common peptides to obtain a long chain of invariant peptide sequences, vi) annotating secondary structure of these conserved peptides from the crystal structure database, vii) comparing pathogenic strain genomes against genomes of non-pathogenic strains and selecting the sequences not commonly conserved in these two groups, viii) validating computationally the invariant sequence motifs as potential drug target sequence by searching for the given conserved sequences in the host genome and rejecting the ones present in the host genome.

In an embodiment to the present invention the length of the sliding window of length 'N' may range from 4 to any length of amino acid residues.

In another embodiment to the present invention the protein sequence data may be taken from any organism but not specifically limited to microbes such as *Mycoplasma pneumoniae, Helicobacter pylori, Hemophillus influenzae, Mycobacterium tuberculosis, Mycoplasma genitalium, Bacillus subtillis, Escherichia coli.*

In further embodiment the conserved peptide motifs as identified comprise:

| | |
|---|---|
| 1. AAQSIGEPGTQLT | (SEQ ID NO:1) |
| 2. AGDGTTTAT | (SEQ ID NO:2) |
| 3. AGRHGNKG | (SEQ ID NO:3) |
| 4. AHIDAGKTTT | (SEQ ID NO:4) |
| 5. CPIETPEG | (SEQ ID NO:5) |
| 6. DEPSIGLH | (SEQ ID NO:6) |
| 7. DEPTSALD | (SEQ ID NO:7) |
| 8. DEPTTALDVT | (SEQ ID NO:8) |
| 9. DHAGIATQ | (SEQ ID NO:9) |
| 10. DHPHGGGEG | (SEQ ID NO:10) |
| 11. DLGGGTFD | (SEQ ID NO:11) |
| 12. DVLDTWFSS | (SEQ ID NO:12) |
| 13. ERERGITI | (SEQ ID NO:13) |
| 14. ERGITITSAAT | (SEQ ID NO:14) |
| 15. ESRRIDNQLRGR | (SEQ ID NO:15) |
| 16. FSGGQRQR | (SEQ ID NO:16) |
| 17. GEPGVGKTA | (SEQ ID NO:17) |
| 18. GFDYLRDN | (SEQ ID NO:18) |
| 19. GHNLQEHS | (SEQ ID NO:19) |
| 20. GIDLGTTNS | (SEQ ID NO:20) |
| 21. GINLLREGLD | (SEQ ID NO:21) |
| 22. GIVGLPNVGKS | (SEQ ID NO:22) |
| 23. GKSSLLNA | (SEQ ID NO:23) |
| 24. GLTGRKIIVDTYG | (SEQ ID NO:24) |
| 25. GPPGTGKTLLA | (SEQ ID NO:25) |
| 26. GPPGVGKT | (SEQ ID NO:26) |
| 27. GSGKTTLL | (SEQ ID NO:27) |
| 28. GTRIFGPV | (SEQ ID NO:28) |
| 29. IDTPGHVDFT | (SEQ ID NO:29) |
| 30. IIAHIDHGKSTL | (SEQ ID NO:30) |
| 31. INGFGRIGR | (SEQ ID NO:31) |
| 32. IREGGRTVG | (SEQ ID NO:32) |
| 33. IVGESGSGKS | (SEQ ID NO:33) |
| 34. KFSTYATWWI | (SEQ ID NO:34) |
| 35. KMSKSKGN | (SEQ ID NO:35) |
| 36. KMSKSLGN | (SEQ ID NO:36) |
| 37. KNMITGAAQMDGAILVV | (SEQ ID NO:37) |
| 38. KPNSALRK | (SEQ ID NO:38) |
| 39. LFGGAGVGKTV | (SEQ ID NO:39) |
| 40. LGPSGCGK | (SEQ ID NO:40) |
| 41. LHAGGKFD | (SEQ ID NO:41) |
| 42. LIDEARTPLIISG | (SEQ ID NO:42) |
| 43. LLNRAPTLH | (SEQ ID NO:43) |
| 44. LPDKAIDLIDE | (SEQ ID NO:44) |
| 45. LPGKLADS | (SEQ ID NO:45) |
| 46. LSGGQQQR | (SEQ ID NO:46) |
| 47. MGHVDHGKT | (SEQ ID NO:47) |
| 48. NADFDGDQMAVH | (SEQ ID NO:48) |
| 49. NGAGKSTL | (SEQ ID NO:49) |
| 50. NLLGKRVD | (SEQ ID NO:50) |
| 51. NTDAEGRL | (SEQ ID NO:51) |
| 52. PSAVGYQPTLA | (SEQ ID NO:52) |
| 53. QRVAIARA | (SEQ ID NO:53) |
| 54. QRYKGLGEM | (SEQ ID NO:54) |
| 55. RDGLKPVHRR | (SEQ ID NO:55) |
| 56. SALDVSIQA | (SEQ ID NO:56) |
| 57. SGGLHGVG | (SEQ ID NO:57) |
| 58. SGSGKSSL | (SEQ ID NO:58) |
| 59. SGSGKSTL | (SEQ ID NO:59) |
| 60. SVFAGVGERTREGND | (SEQ ID NO:60) |
| 61. TGRTHQIRVH | (SEQ ID NO:61) |
| 62. TGVSGSGKS | (SEQ ID NO:62) |
| 63. TLSGGEAQRI | (SEQ ID NO:63) |
| 64. TNKYAEGYP | (SEQ ID NO:64) |
| 65. TPRSNPATY | (SEQ ID NO:65) |
| 66. VEGDSAGG | (SEQ ID NO:66) |
| 67. VRKRPGMYIG | (SEQ ID NO:67) |

In yet another embodiment to the present invention, the number of invariant peptides may vary according to the relatedness among the organisms and the number of organisms being compared.

In still another embodiment, the invariant sequences may belong to the following proteins as available in a public database such as one maintained by the National Center For Biotechnology Information (NCBI), wherein the said list of proteins comprise:

I DNA DIRECTED RNA POLYMERASE BETA CHAIN
II EXCINUCLEASE ABC SUBUNIT A
III EXCINUCLEASE ABC SUBUNIT B
IV DNA GYRASE SUBUNIT B
V ATP SYNTHASE BETA CHAIN
VI S-ADENOSYLMETHIONINE SYNTHETASE
VII GLYCERALDEHYDE 3-PHOSPHATE DEHYDROGENASE
VIII ELONGATION FACTOR G (EF-G)
IX ELONGATION FACTOR TU (EF-TU)
X 30S RIBOSOMAL PROTEIN S12
XI 50S RIBOSOMAL PROTEIN L12
XII 50S RIBOSOMAL PROTEIN L14
XIII VALYL tRNA SYNTHETASE (VALRS)
XIV CELL DIVISON PROTEIN FtSH HOMOLOG
XV DnaK PROTEIN (HSP70)
XVI GTP BINDING PROTEIN LepA
XVII TRANSPORTER
XVIII OLIGOPEPTIDE TRANSPORT ATP BINDING PROTEIN OPPF

In still another embodiment to the present invention, the said method of comparing the peptide libraries as given in step (iii) of method explained above is carried out by following the steps given in FIG. 1.

In yet another embodiment to the present invention, the said method of locating the common peptides in the original protein sequences as given in step (iv) method explained above is carried out by following the steps given in FIG. 2.

In another embodiment, the method of creating a common peptide of variable length after removing the overlappings as given in step (v) of method explained above is carried out by following the steps given in FIG. 3.

In another embodiment to the present invention, the microprocessor based system for performing the methods of the invention comprises:

i) means of determining the amino acid sequence window for creation of peptide library and subsequent sorting,
ii) means of comparing the peptide library,
iii) locating computationally these common peptides in the original proteins and subsequently labeling them with their origin and location,
iv) joining computationally the overlapping common peptides to obtain a long chain of invariant peptide sequences, In another embodiment of the invention, the computer system for performing the methods of the invention comprises, a central processing unit, executing peptide library creating program (PEPLIB), peptide library matching program (PEPLIMP), peptide stitching program (PEPSTITCH), peptide extraction program (PEPXTRACT) wherein the said programs are all stored in a memory device accessed by the central processing unit connected to a display on which the central processing unit displays the screens of the above mentioned programs in response to user inputs with a user interface device.

In yet another embodiment to the present invention, the method for assigning function to a protein of unknown function showing no/weak homology to other protein sequences in a publicly available database (SWISSPROT) may be carried out by employing the following steps:
I. generating computationally overlapping peptide library from the protein sequences of unknown function,
II. sorting computationally the peptides of length 'N' (N is the length of the sliding window of amino acids) obtained as above, alphabetically, according to single letter amino acid code,
III. matching computationally the current library with peptide library of all functionally known proteins to obtain common peptides,
IV. locating computationally these common peptides in the original proteins and subsequently labeling them with their origin and location,
V. joining computationally the overlapping common peptides to obtain a long chain of invariant peptide sequences,
VI. assigning function to the unknown protein based on the function of the protein with which maximum length of peptide sequence identity is found. The more is the number of matches with the proteins of similar function the likelihood of functional assignment will be higher.

The particulars of the organisms such as their name, strain, accession number and other details are given below.

| Genomes | Strain | Accession Number | Total Base Sequences | Date of Completion |
|---|---|---|---|---|
| *Mycobacterium tuberculosis* Cole, S. T., and et.al. Nature 393 (6685), 537-544 (1998) | H37Rv. | AL123456 | 4411529 bp | Jun. 11, 1998. |
| *Bacillus subtilis* Kunst, F. and et.al. Nature 390 (6657), 249-256 (1997) | DY | AL009126 | 4214814 bp | Nov. 20, 1997 |
| *Mycoplasma genitalium* Fraser, C. M., and et.al. Science 270 (5235), 397-403 (1995) | G37 | L43967 | 580074 bp | Oct. 30, 1995 |
| *Mycoplasma pneumonia* Himmelreich, R., and et.al Nucleic Acids Res. 24 (22), 4420-4449 (1996) | M129 | U00089 | 816394 bp | Nov. 15, 1996 |
| *Escherichia coli* Blattner, F. R.,. and et.al Science 277 (5331), 1453-1474 (1997) | K-12 | U00096 | 4639221 bp | Oct. 13, 1998. |
| *Helicobacter pylori* Tomb, J.-F., and et.al Nature 388 (6642), 539-547 (1997) | 26695 | AE000511 | 1667867 bp | Aug. 6, 1997. |
| *Haemophilus influenzae* Fleischmann, R. D., and et.al Science 269 (5223), 496-512 (1995) | Rd | L42023 | 1830138 bp | Jul. 25, 1995. |

| Genome | Proteins | Number of 8-mer peptides | No. of Proteins in which common peptides are found |
|---|---|---|---|
| *Bacillus subtilis* | 4100 | 1174826 | 69 |
| *Escherichia coli* | 4289 | 1302149 | 81 |
| *Haemophilus influenzae* | 1709 | 504044 | 56 |
| *Helicobacter pylori* | 1566 | 474087 | 51 |
| *Mycoplasma genitalium* | 467 | 165523 | 30 |
| *Mycoplasma pneumonia* | 677 | 221216 | 43 |
| *Mycobacterium tuberculosis* | 3918 | 1252582 | 58 |

BRIEF DESCRIPTION OF THE ACCOMPANYING DRAWINGS

The invention is explained with the help of the following examples and should not be constructed to limit the scope of the present invention.

EXAMPLES

Example 1

1. The Peptide Library Creation Program (PEPLIB)

The purpose of the program is to create a non-redundant peptide library of user specified window length 'N' of a given genome by sliding the window by one amino acid residue at a time. The program works as follows:

The internet downloaded FASTA format files obtained from the National Center For Biotechnology Information (NCBI), database were saved by the name <organism_name>.pep and passed as input to the PERL program which creates the unique peptides of length as specified at the time of execution.

Input/Output file format:
 Downloaded Files and their format:
  <organism_name>.pep:file which stores the annotation & the protein sequence <organism-name> refers to
  Tb (*Mycobacterium tuberculosis*) Bs (*Bacillus subtilis*) Mg (*Mycoplasma genitalium*) Mp (*Mycoplasma pneumonoia*) Ec (*Escherichia coli*) Hp (*Helicobacter pylori*) Hi (*Haemophilus influenzae*)
  Format: FASTA
  ">gi|"<annotation>
  <<the entire protein sequence . . .
  For example,
  >gi|2808711|emb|CAA16238.1|dnaA
  MTDDPGSGFTTVWNAVVSELNGDP-KVDDGPSSDANLSAPLTPQQRAWLNLVQPLTIVE GFALLSVPSSFVQNEIERHLRAPIT-DALSRRLGHQIQLGVRIAPPATDEADDT-TVPPSENP ATTSPDTTDNDEIDDSAAARGDNQH-SWP . . . (SEQ ID NO:68)
  >gi|3261513|emb|CAA16239.1|dnaN
  MDAATTRVGLTDLTFRLLRESFADAVSW-VAKNLPARPAVPVLSGVLLTGSDNGLTISGF DYEVSAEAQVGAEIVSPGSVLVSGRLLS-DITRALPNKPVDVHVEGNRVALTCGNARFSL PTMPVEDYPTLPTLPEETGLLPAE . . . (SEQ ID NO:69)

The output file: <organism_name><peptide_length>.txt
Format:
<all unique peptides of length specified at the time of execution>for example format of Tb8.txt:

AAAAAAAA

AAAAAAAG

AAAAAAAQ

AAAAAAAS

AAAAAAAT

Example 2

The Peptide Library Matching Program (PEPLIMP)

Figure 1:
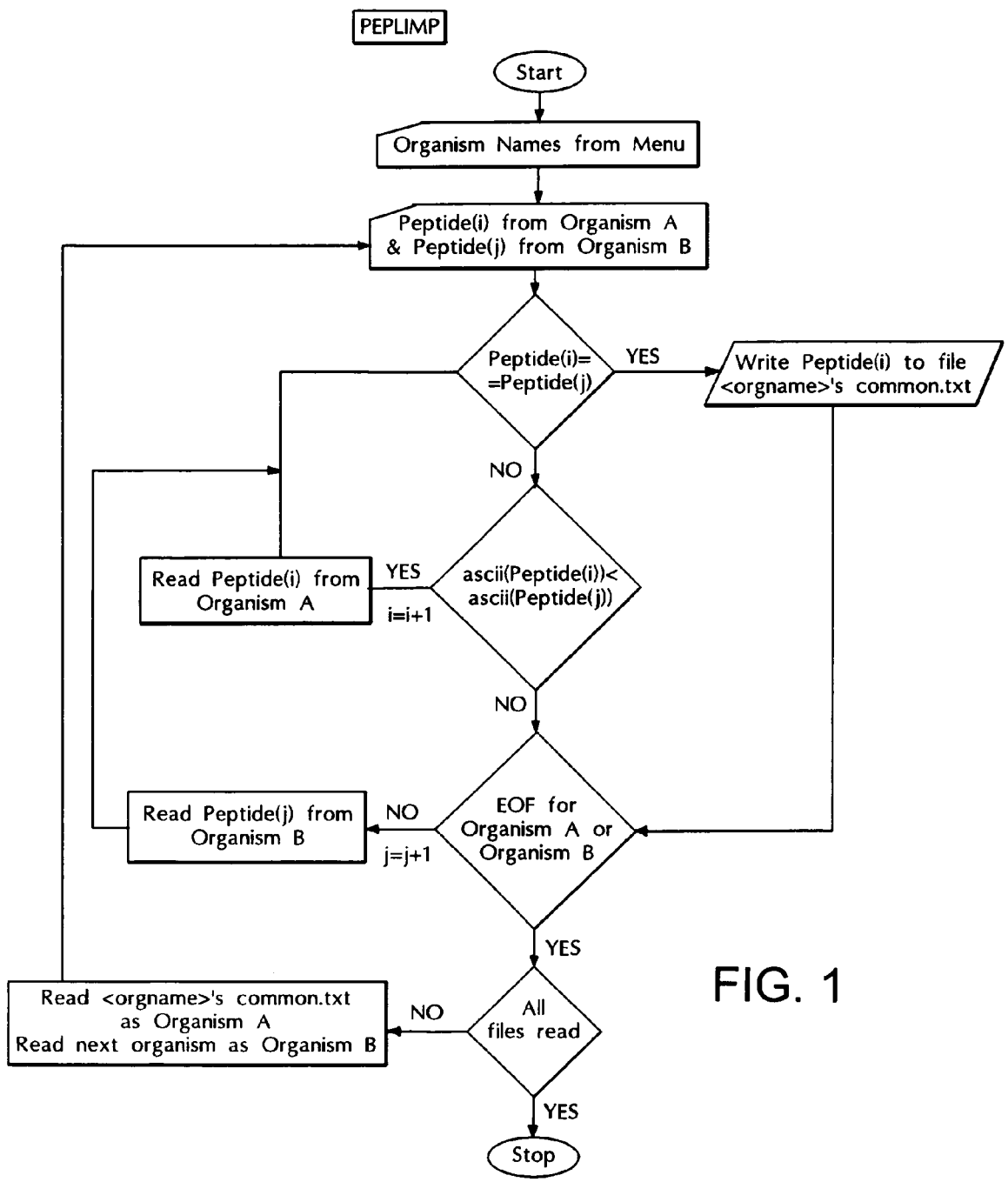
FIG. 1 shows a logic circuit of Peptide Library Matching Program.

The purpose of the program is to compare the user defined peptide libraries with each other and report the common/unique peptides. The output files of the program PEPLIB are used as input for the PEPLIMP program. As the program is executed the user is prompted to select the libraries that are to be compared. Depending upon the libraries selected an output file is generated having common peptides (FIG. 1). Comparison of 8-mer peptide libraries of the above mentioned seven organisms resulted into 164 eight-mer peptides.

Comparison of four pathogenic organisms such as *Mycobacterium tuberculosis, Helicobacter pylori, Mycoplasma pneumonia* and *Haemophilus influenzae* resulted in 206 invariant peptides and comparison of three non-pathogenic organisms such as *Bacillus subtilis, Mycoplasma genitalium* and *Escherichia coli* resulted in 601 invariant peptides. The comparison tree looks like:

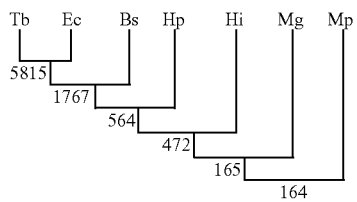

Example 3

The Peptide Extraction Program (PEPXTRACT)

Figure 2:
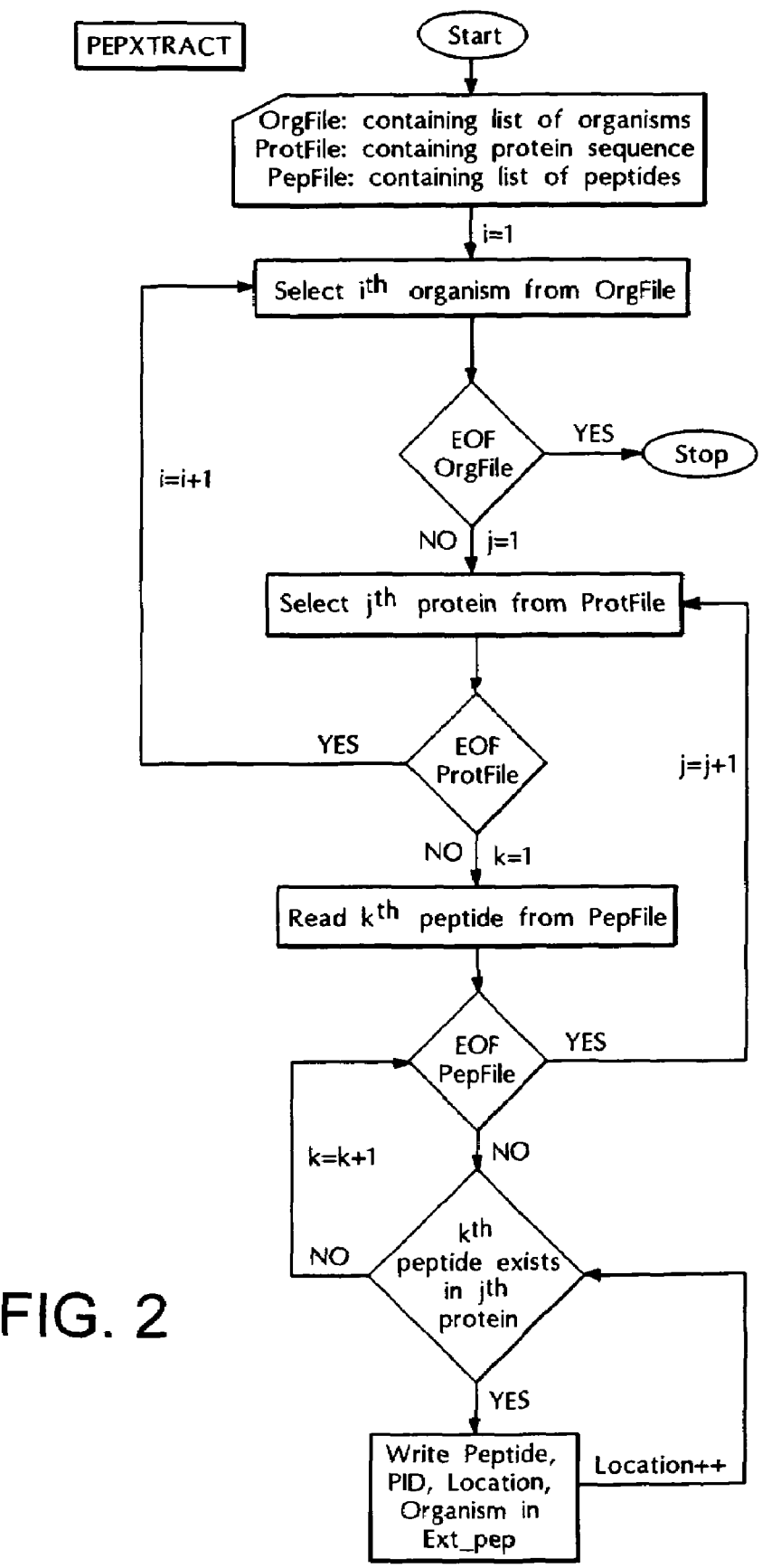
FIG. 2 shows a Logic circuit of Peptide Extraction Program.

This program takes the output of PEPLIMP program i.e., all the invariant peptides as input and locates these peptides in the protein sequences from the original database and labels them with the protein identification number (PID), location and organism name for further analysis. The logic circuit of this program is explained in the flow chart shown in FIG. 2.

Example 4

The Peptide Stitching Program (PEPSTITCH)

Figure 3:
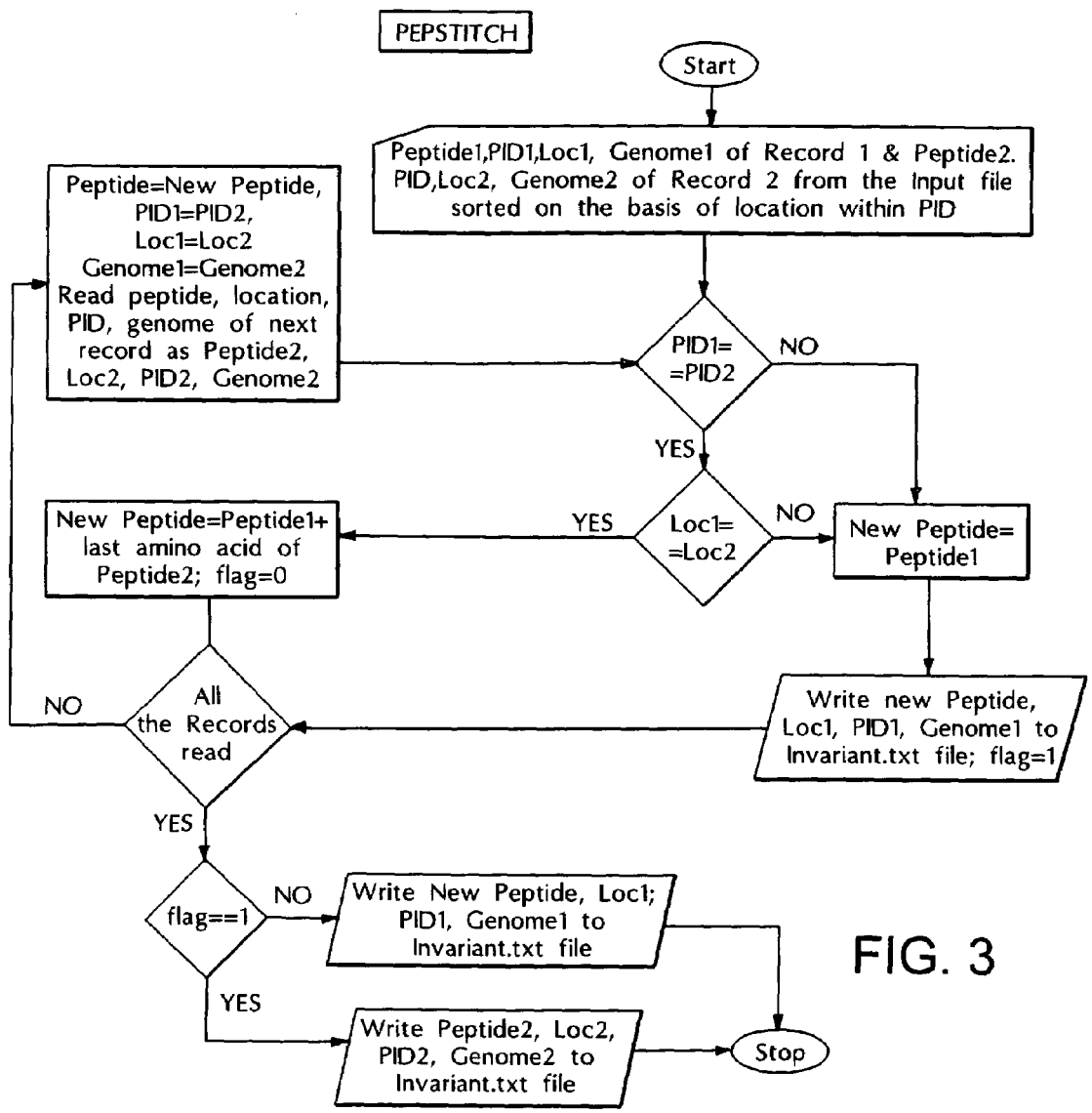
FIG. 3 shows a Logic circuit of Peptide Stitching Program.

This program intelligently removes the overlapping invariant peptides and reports all the continuous stretch of invariant peptide present in the protein under consideration. This is done by first grouping the 'N'-mer peptides from the same protein of an organism and then keeping track on the their location they are merged into a long single peptide. The logic circuit of this program is shown in FIG. 3.

Example 5

Prediction Of Function Of Hypothetical Protein

An invariant peptide having sequence FSGGQRQR (SEQ ID NO:16) was found to exist in oppF/dppF proteins of six organisms out of the seven examined (except for in *M. tuberculosis*). This protein functions as an ATP binding protein. Since this invariant peptide has also been found to be located on the hypothetical protein encoded by Rv1273c gene in *M. tuberculosis*, it is suggested that this protein encoded by Rv1273c gene must function as ATP binding protein as it holds the signature of this class of protein.

Example 6

Prediction Of Function Of Hypothetical Protein

Another invariant peptide having sequence GIVGLPN-VGKS (SEQ ID NO:22) was found in proteins having GTP binding function in six bacteria out of the seven examined (except for in *M. tuberculosis*) where as the same invariant sequence is present in hypothetical protein encoded by Rv1112 protein in *M. tuberculosis*. It is strongly suggested that this hypothetical protein may have GTP binding property as it holds the signature of this class of protein.

Example 7

Drug Target Identification Based On Invariant Peptide Motifs

Figure 4:
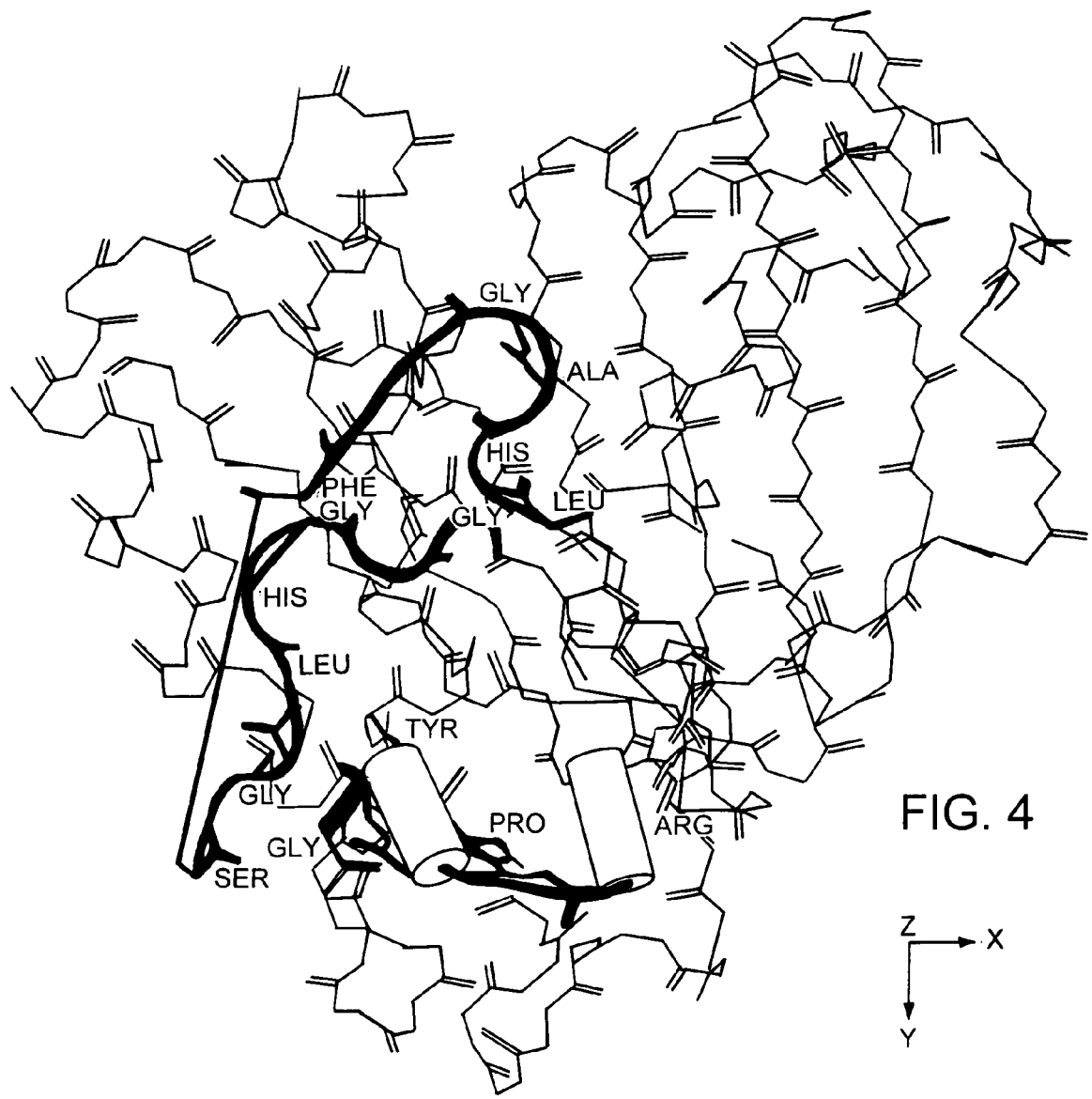
FIG. 4 shows crystal structures of three invariant peptides (VRKRPGMYIG (SEQ ID NO:67), LHAGGKFD (SEQ ID NO:41) and SGGLHGVG (SEQ ID NO:57)) from DNA gyrase B protein.

Enzyme DNA gyrase is known to reduce supercoiling of DNA. This protein is absent in human and has been considered as a potential drug target. However, the exact sequence to which the drug molecules should be targeted is not yet clear. The peptides such as VRKRPGMYIG (SEQ ID NO:67), LHAGGKFD (SEQ ID NO:41), SGGLHGVG (SEQ ID NO:57), LPGKLADC (SEQ ID NO:45), VEGDSAGG (SEQ ID NO:66) and QRYKGLGEM (SEQ ID NO:54) that are invariant across many pathogenic and non-pathogenic bacterial DNA gyrase beta subunit, but absent in host, are the structural determinants which could be used as potential drug targets against bacterial infections. The crystal structures of three of these peptides are shown in FIG. 4.

Example 8

Assignment Of A Function To A Protein Of Unknown Function

With the help of this method one can assign function to a protein of unknown function showing no/weak homology to other protein sequences in a publicly available database (SWISSPROT) by employing the following steps:
  I. generating computationally overlapping peptide library from the protein sequences of unknown function,
  II. sorting computationally the peptides of length 'N' (N is the length of the sliding window of amino acids) obtained as above, alphabetically, according to single letter amino acid code, III. matching computationally the current library with peptide library of all functionally known proteins to obtain common peptides, IV. locating computationally these common peptides in the original proteins and subsequently labeling them with their origin and location, V. joining computationally the overlapping common peptides to obtain a long chain of invariant peptide sequences, VI. assigning function to the unknown protein based on the function of the protein with which maximum length of peptide sequence identity is found. The more is the number of matches with the proteins of similar function the likelihood of functional assignment will be higher.

ADVANTAGES

1. Main advantage of the present invention is to provide a new method of genome-wise comparison of large number (thousands) of proteins of one organism with proteins of other organisms simultaneously to arrive at invariant peptide sequence motif signatures.

2. It provides a rapid method of identification of invariant peptide motifs.

3. It provides a simple and highly accurate method of determining invariant peptide motifs as it does not involve any complex mathematical calculations.

4. It provides a basis for a screening assay for broad-spectrum antibacterial compounds.

REFERENCES

Altschul, S. F., Carol, R. J., & Lipman, D. J. (1990). Basic local alignment search tool. J.Mol.Biol. 215, 403-410.

Cutler N. S., Heitman J., Cardenas M. E., (1999). TOR kinase homologs function in a signal transduction pathway that is conserved from yeast to mammals. Mol Cell Endocrinol 155(1-2), 135-142.

Ghannoum, M. A. and Rice, L. B., (1999). Antifungal agents: mode of action, mechanisms of resistance, and correlation of these mechanisms with bacterial resistance. Clin Microbiol Rev 12(4), 501-517.

McCafferty D. G., Cudic, P., Yu, M. K., Behenna, D. C., Kruger, R., (1999). Synergy and duality in peptide antibiotic mechanisms. Curr Opin Chem Biol 3(6), 672-680.

Porse, B. T., & Garrette. R. A.(1999).Ribosomal mechanics, antibiotics, and GTP hydrolysis. Cell 97, 423-426.

Presenell, S. R., Cohen, B. I., & Cohen, F. E., (1992). A segment based approach to protein secondary structure prediction. Biochemistry 31, 983-993.

Rooman, M. J., & Wodak, S. J. (1988). Identification of predictive sequence motifs limited by protein structure database size. Nature 335, 45-49.

Wilbur W. J., & Lipman, D. J. (1983). Rapid similarity searches of nucleic acid and protein data banks. Proc Natl Acad Sci USA 80, 726-730.

Wimberly, B. T., Guymon, R., McCutcheon, White, S. W., & Ramakrishnan, V., (1999). A etailed view of a ribosomal active site: The structure of the L11-RNA complex. Cell 97, 491-502.

We claim:

1. A computer-based method for identifying conserved peptide motifs useful as drug targets for use in a host organism, wherein said method comprises the steps of:
   i) computationally generating using one or more computer processors overlapping peptide sequences of length 'N' from selected pathogenic organisms using a peptide library creating software program (PEPLIB),
   ii) computationally sorting the peptide sequences of length 'N' according to amino acid sequence,
   iii) computationally matching using one or more computer processors the sorted peptide sequences of length 'N' of the selected pathogenic organisms to produce exactly matched common peptide sequences using a peptide library matching software program (PEPLIMP),
   iv) computationally locating the matched common peptide sequences in their corresponding protein sequences to provide locations of said matched common peptide sequences and subsequently labeling the matched common peptide sequences with their origin and location using a peptide extraction software program (PEPEXTRACT);
   v) computationally joining overlapping common peptide sequences to obtain extended conserved peptide sequences using a peptide stitching software program (PEPSTITCH);
   vi) comparing said extended conserved peptide sequences obtained in step (v) to host organism protein sequences to identify conserved peptide sequences from said selected pathogenic organisms which are not present in host proteins; and
   vii) communicating said conserved peptide sequences from said selected pathogenic organisms not present in said host proteins to a user to obtain conserved peptide motifs useful as drug targets for use in a host organism, wherein all of said steps are performed on a computer.

2. The method of claim 1, wherein 'N' is at least 4.

3. The method of claim 1 wherein the selected pathogenic organisms include at least one of: *Mycoplasma pneumoniae, Helicobacter pylori, Hemophilus influenzae, Mycobacterium tuberculosis, Mycoplasma genitalium, Bacillus subtilis*, and *Escherichia coli*.

4. The method of claim 1, wherein the extended conserved peptide sequences comprise one or more of the following sequences:

```
 1. AAQSIGEPGTQLT    (SEQ ID NO:1)
 2. AGDGTTTAT        (SEQ ID NO:2)
 3. AGRHGNKG         (SEQ ID NO:3)
 4. AHIDAGKTTT       (SEQ ID NO:4)
 5. CPIETPEG         (SEQ ID NO:5)
 6. DEPSIGLH         (SEQ ID NO:6)
 7. DEPTSALD         (SEQ ID NO:7)
 8. DEPTTALDVT       (SEQ ID NO:8)
 9. DHAGIATQ         (SEQ ID NO:9)
10. DHPHGGGEG        (SEQ ID NO:10)
11. DLGGGTFD         (SEQ ID NO:11)
12. DVLDTWFSS        (SEQ ID NO:12)
13. ERERGITI         (SEQ ID NO:13)
14. ERGITITSAAT      (SEQ ID NO:14)
15. ESRRIDNQLRGR     (SEQ ID NO:15)
16. FSGGQRQR         (SEQ ID NO:16)
17. GEPGVGKTA        (SEQ ID NO:17)
18. GFDYLRDN         (SEQ ID NO:18)
19. GHNLQEHS         (SEQ ID NO:19)
20. GIDLGTTNS        (SEQ ID NO:20)
21. GINLLREGLD       (SEQ ID NO:21)
22. GIVGLPNVGKS      (SEQ ID NO:22)
23. GKSSLLNA         (SEQ ID NO:23)
24. GLTGRKIIVDTYG    (SEQ ID NO:24)
25. GPPGTGKTLLA      (SEQ ID NO:25)
26. GPPGVGKT         (SEQ ID NO:26)
27. GSGKTTLL         (SEQ ID NO:27)
28. GTRIFGPV         (SEQ ID NO:28)
29. IDTPGHVDFT       (SEQ ID NO:29)
30. ILAHIDHGKSTL     (SEQ ID NO:30)
31. INGFGRIGR        (SEQ ID NO:31)
32. IREGGRTVG        (SEQ ID NO:32)
33. IVGESGSGKS       (SEQ ID NO:33)
34. KFSTYATWWI       (SEQ ID NO:34)
35. KMSKSKGN         (SEQ ID NO:35)
36. KMSKSLGN         (SEQ ID NO:36)
37. KNMITGAAQMDGAIL  (SEQ ID NO:37)
38. KPNSALRK         (SEQ ID NO:38)
39. LFGGAGVGKTV      (SEQ ID NO:39)
40. LGPSGCGK         (SEQ ID NO:40)
41. LHAGGKFD         (SEQ ID NO:41)
42. LIDEARTPLIISG    (SEQ ID NO:42)
43. LLNRAPTLH        (SEQ ID NO:43)
44. LPDKAIDLIDE      (SEQ ID NO:44)
45. LPGKLADC         (SEQ ID NO:45)
46. LSGGQQQR         (SEQ ID NO:46)
47. MGHVDHGKT        (SEQ ID NO:47)
48. NADFDGDQMAVH     (SEQ ID NO:48)
49. NGAGKSTL         (SEQ ID NO:49)
50. NLLGKRVD         (SEQ ID NO:50)
51. NTDAEGRL         (SEQ ID NO:51)
52. PSAVGYQPTLA      (SEQ ID NO:52)
```

-continued

```
53. QRVALARA          (SEQ ID NO:53)
54. QRYKGLGEM         (SEQ ID NO:54)
55. RDGLKPVHRR        (SEQ ID NO:55)
56. SALDVSIQA         (SEQ ID NO:56)
57. SGGLHGVG          (SEQ ID NO:57)
58. SGSGKSSL          (SEQ ID NO:58)
59. SGSGKSTL          (SEQ ID NO:59)
60. SVFAGVGERTREGND   (SEQ ID NO:60)
61. TGRTHQIRVH        (SEQ ID NO:61)
62. TGVSGSGKS         (SEQ ID NO:62)
63. TLSGGEAQRI        (SEQ ID NO:63)
64. TNKYAEGYP         (SEQ ID NO:64)
65. TPRSNPATY         (SEQ ID NO:65)
66. VEGDSAGG          (SEQ ID NO:66);
and
67. VRKRPGMYIG        (SEQ ID NO:67)
```

5. The method of any one of claims 1-4 wherein the conserved peptide sequences are found within the sequences of at least one of the following proteins:

I DNA DIRECTED RNA POLYMERASE BETA CHAIN
II EXONUCLEASE ABC SUBUNIT A
III EXONUCLEASE ABC SUBUNIT B
IV DNA GYRASE SUBUNIT B
V ATP SYNTHASE BETA CHAIN
VI S-ADENOSYLMETHIONINE SYNTHETASE
VII GLYCERALDEHYDE 3-PHOSPHATE DEHYDROGENASE
VIII ELONGATION FACTOR G (EF-G)
IX ELONGATION FACTOR TU (EF-TU)
X 30S RIBOSOMAL PROTEIN S12
XI 50S RIBOSOMAL PROTEIN L12
XII 50S RIBOSOMAL PROTEIN L14
XIII VALYL tRNA SYNTHETASE
XIV CELL DIVISION PROTEIN FtSH HOMOLOG
XV DnaK PROTEIN (HSP70)
XVI GTP BINDING PROTEIN LepA; and
XVII OLIGOPEPTIDE TRANSPORT ATP BINDING PROTEIN OPPF.

6. The method of claim 1, wherein step (iii) comprises:
selecting organism names from a menu;
iteratively comparing peptide sequences of a first organism to sorted peptide sequences of a second organism; and
writing matched sequences to a first file for the first organism and to a second file for the second organism.

7. The method of claim 1 wherein step (iv) comprises:
selecting protein sequences;
iteratively locating matched peptide sequences in the selected protein sequences; and
if the matched peptide is found in one of the selected protein sequences, labeling the matched peptide sequence in a file associated with the selected protein sequence with: a) a protein identification number (PID), b) a location in the protein sequence, and c) a name of a pathogenic organism chosen from the group of selected pathogenic organisms of step iii).

8. The method of claim 1, wherein said overlapping common peptide sequences in step (v) are computationally joined by:
iteratively comparing matched peptide sequences on matched peptide locations;
determining overlapping matched common peptides; and
determining extended conserved peptide sequences based on overlapping matched common peptides.

* * * * *